United States Patent [19]

Walsh et al.

[11] 4,230,718
[45] Oct. 28, 1980

[54] 1-SUBSTITUTED-3,4-EPOXYPYRROLI-DINES

[75] Inventors: David A. Walsh; William J. Welstead, Jr., both of Richmond, Va.

[73] Assignee: A. H. Robins Company, Inc., Richmond, Va.

[21] Appl. No.: 2,150

[22] Filed: Jan. 9, 1979

[51] Int. Cl.$^3$ .................. C07D 295/02; C07D 209/00
[52] U.S. Cl. .............................. 424/274; 260/326.5 B
[58] Field of Search .................. 260/326.5 B; 424/274

[56] References Cited
U.S. PATENT DOCUMENTS 3,657,274   4/1972   Ohki et al. ..................... 260/326.5 B Primary Examiner—Jose Tovar

[57] ABSTRACT

3,4-Epoxypyrrolidines substituted in the 1-position with alkyl, cycloalkyl and phenylalkyl are disclosed which have pharmaceutical application in cataract prevention in animals and as intermediates in preparation of trans-3-aryloxy-4-hydroxypyrrolidines. The epoxypyrrolidines are prepared by a novel route involving chlorination of pyrrolines in aqueous medium.

22 Claims, No Drawings

1-SUBSTITUTED-3,4-EPOXYPYRROLIDINES

BACKGROUND OF THE INVENTION

1. Field of Invention

The present invention relates to certain novel 1-substituted-3,4-epoxypyrrolidines, a novel method for making and novel pharmaceutical use therefor. More particularly the invention relates to novel 1-substituted-3,4-epoxypyrrolidines, a novel process for producing the epoxypyrrolidines via 1-substituted pyrroline and a method of treatment for prevention and treatment of various diabetic complications including inhibition of sugar cataract formation in animals. The epoxypyrrolidines are also useful in preparation of 3-aryloxy-4-hydroxypyrrolidine which are described in a copending application filed on even date herewith.

2. Description of the Prior Art

Compounds of the present invention have not heretofore been available as no method of making the 1-substituted epoxypyrrolidines of the present invention was known. 1-Acyl-3,4-epoxypyrrolidines have been prepared by Oida, S. and Ohki, E. in Chem. Pharm. Bull. (Tokyo) 1969 17(5) 980-6; Chem. Abstracts 71, 49688k.

SUMMARY OF INVENTION

The present invention provides novel 1-substituted-3,4-epoxypyrrolidines, a novel method of producing and a novel use therefor.

The compounds of the invention are represented by the following general structure formula:

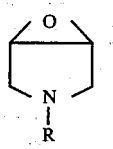

Formula I wherein R is lower alkyl, cycloalkyl and phenylalkyl and the acid addition salts thereof.

The novel process for producing the N-substituted-3,4-epoxypyrrolidines of the present invention as described more fully hereinbelow relies on conversion of the 1-R-substipyrrolines to intermediate 3-hydroxy-4-chloro-1-substituted pyrrolidine with chlorine under acid conditions in an aqueous medium. The intermediate is converted to the 1-substituted-3,4-epoxypyrrolidines of Formula I.

The novel method of inhibiting cataract formation by reducing aldose reductase and alditol formation in the lens of eyes in animals by administering the 1-substituted-3,4-epoxypyrrolidines of Formula I and pharmaceutically acceptable acid addition salts thereof is also part of the present invention. J. H. Kinoshita, Invest. Ophthal. 4, 786 (1965) has demonstrated that an agent which is capable of inhibiting aldose reductase can prevent detrimental accumulation of dulcitol in the lens which leads to cataracts.

The compounds of Formula I also have utility in producing trans-3-aryloxy-4-hydroxypyrrolidines which are antidepressants. This utility relies on reactivity of arylhydroxy compounds with the 1-substituted-3,4-epoxypyrrolidines to produce the trans-3-aryloxy-4-hydroxypyrrolidines.

Accordingly, it is an object of the present invention to provide novel 1-substituted-3,4-epoxypyrrolidines which have utility as pharmacological agents and chemical intermediates.

Another object is to provide a novel method of producing 1-substituted-3,4-epoxypyrrolidines.

Still another object is to provide a method of reducing aldose reductase, leading to inhibition of cataract fromation in diabetic animals.

Additional objects will be apparent to one skilled in the art and still other objects will become apparent hereinafter.

DETAILED DESCRIPTION OF THE INVENTION

The present invention encompasses the 1-substituted-3,4-epoxypyrrolidines of Formula I, the method of producing same and a method of inhibiting cataracts in animals.

In the definition of terms as used herein in the specification and claims:

The term "lower-alkyl" includes straight and branched chain radicals of up to eight carbon atoms inclusive and is exemplified by such groups as methyl, ethyl, propyl, isopropyl, butyl, isobutyl, tertiary butyl, amyl, isoamyl, hexyl, heptyl, octyl and the like.

By cycloalkyl is meant cycloalkyl radicals having 3 to 9 carbon atoms and includes such radicals as cyclopropyl, cyclobutyl, cyclopentyl, cyclohexyl and the like.

Representative of phenyl-alkyl radicals are α-methylbenzyl, phenylethyl, phenylpropyl, phenylbutyl and the like.

The pyrroline materials used in preparation of compounds of Formula I are prepared by generally known methods according to the procedure of U.S. Pat. No. 3,691,198 as represented by the following equation:

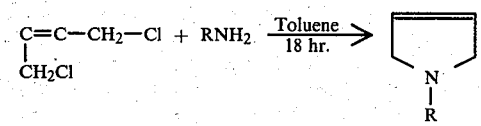

Formula II

The synthesis of one compound of Formula II not previously reported; namely, 1-cyclohexyl-Δ³-pyrroline, is given in Preparation 1.

PREPARATION 1

1-Cyclohexyl-Δ³-pyrroline

A solution of 5.19 kg (52.3 moles) of cyclohexylamine in 4.0 liters of benzene was heated to mild reflux (92° C.) and then heating discontinued. To the solution was added, dropwise, 1,635 g (13.1 moles) of 1,4-dichlorobutene at a rate sufficient to maintain gentle reflux, 3 hours time being required. Heating was continued and the reactants were heated at reflux temperature for 18 hours. The mixture was cooled to about 50° C. and filtered to remove the hydrochloric acid salt. Carbon dioxide was bubbled into the filtrate to precipitate excess amine carbonate salt which was removed by filtration. Solvent was removed from the filtrate by distillation under reduced pressure and the reddish fluid residue slightly contaminated with benzene weighed 1,506 g (76% yield).

The novel synthesis of the novel 1-substituted-3,4-epoxypyrrolidines of the present invention is accomplished by reacting the 1-substituted-$\Delta^3$-pyrrolines with chlorine in aqueous acidic medium and thereafter causing epoxidation with base as represented by the following equation:

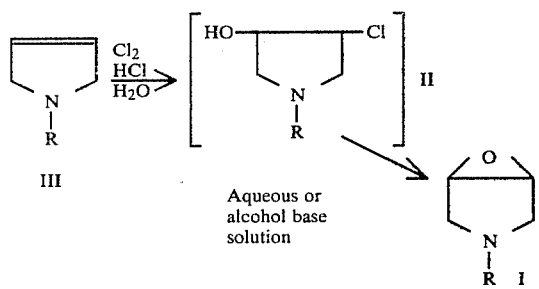

wherein R is as defined hereinabove. Generally, the chlorination step is accomplished in 2–6 hours and the intermediate II need not be isolated. Crude epoxypyrrolidines are obtained by solvent extraction and converted to crystalline salt such as oxalate. Pure free base of the epoxides may be obtained from the oxalate salt by partitioning between 5% aqueous sodium carbonate and methylene chloride and thereafter drying over anhydrous sodium sulfate and evaporating methylene chloride.

The novel compounds of the present invention and the novel process is exemplified more fully by the following illustrative examples. The scope of the invention is, however, not limited thereto.

EXAMPLE 1

1-Benzyl-3,4-epoxypyrrolidine Oxalate

A mixture of 31.8 g (0.20 mole) of 1-benzyl-$\Delta^3$-pyrroline, 25.1 of concentrated hydrochloric acid and 300 ml. of water was treated with a stream of chlorine for 2 hr. The solution was filtered and the filtrate was made basic with 20% sodium hydroxide. The basic solution was extracted with three 150-ml. portions of methylene chloride. The combined methylene chloride extracts were dried over magnesium sulfate and evaporated to give 48.5 g. of crude chlorohydrin as a dark oil. This oil was stirred with 200 ml. of 20% sodium hydroxide for 0.5 hr., 700 l. of water was added, and the base was extracted with four 100-ml portions of methylene chloride. The combined methylene chloride extracts were dried over magnesium sulfate and concentrated to yield 34.9 g. (99%) of crude epoxide as a dark oil. The oxalate salt was prepared in 81% yield. Recrystallization from 95% ethanol gave the salt as off-white needles, m.p. 148°–49°/d.

Analysis: Calculated for $C_{13}H_{15}NO_5$: C, 58.86; H, 5.70; N, 5.28. Found: C, 58.55; H, 5.68; N, 5.25.

EXAMPLE 2

1-Ethyl-3,4-epoxypyrrolidine Oxalate

A mixture of 61 g. (0.63 mole) of 1-ethyl-$\Delta^3$-pyrroline, 50 ml. of concentrated aqueous hydrochloric acid, and 600 ml. of water was treated with chlorine gas for 2.5 hr. The mixture was filtered through cotton and the filtrate was washed with two 100-ml. portions of methylene chloride. The aqueous layer was made basic with 20% sodium hydroxide, heated on a steam bath for 0.5 hr., and extracted with three 100-ml. portions of methylene chloride. The combined extracts were dried over anhydrous sodium sulfate and concentrated and the residue vacuum distilled to give 39.4 g. (56%) of the epoxide as a clear oil (b.p. 75°–90° at 28 mm.). The epoxide was converted to the oxalate and the salt was recrystallized from absolute ethanol to give the product as white needles, m.p. 142°–4° d.

Analysis: Calculated for $C_8H_{13}NO_5$: C, 47.29; H, 6.45; N, 6.89. Found: C, 47.12; H, 6.42; N, 6.82.

EXAMPLE 3

1-Cyclohexyl-3,4-epoxypyrrolidine Oxalate

A solution of 151.3 g. (1.0 mole) of 1-cyclohexyl-$\Delta^3$-pyrroline, 100 ml of concentrated hydrochloric acid and 1.8 liters of water was treated with a stream of chlorine gas until uptake ceased (~6 hrs). The solution was washed with methylene chloride and the acidic solution was left standing overnight. The solution was then made basic with 50% sodium hydroxide and extracted with methylene chloride. The combined extracts were concentrated to give 185 g. of chlorohydrin as residue. The residue was slowly poured into a 20% sodium hydroxide/ethanol solution. The mixture was stirred for 0.5 hour and then 3.5 liters of water was added. The mixture was extracted with methylene chloride and the combined extracts were dried over anhydrous sodium sulfate and concentrated to give 154 g. (92%) of amine epoxide. An nmr analysis indicates this residue is 86% epoxide and 14% 3,4-dichloro-N-cyclohexylpyrrolidine. The residue was vacuum distilled to give the epoxide as a water-white liquid, bp 71° @ 0.6 mm. A portion of the liquid was converted to the oxalate to give a white solid, mp. 155°–6° d (absolute EtOH).

Analysis: Calculated for $C_{12}H_{19}NO_5$: C, 56.02; H, 7.44; N, 5.44. Found: C, 56.05; H, 7.50; N, 5.34.

EXAMPLE 4

Following the procedure of Example 1 and substituting molar equivalent amounts of the following pyrrolines for 1-benzyl-$\Delta^3$-pyrroline:
1-phenyethyl-$\Delta^3$-pyrroline
1-α-methylbenzyl-$\Delta^3$-pyrroline
there are obtained:
1-phenylethyl-3,4-epoxypyrrolidine
1-α-methylbenzyl-3,4-epoxypyrrolidine.

EXAMPLE 5

Following the procedure of Example 2, substituting molar amounts of the following pyrrolines for 1-ethyl-$\Delta^3$-pyrroline:
1-isopropyl-$\Delta^3$-pyrroline
1-methyl-$\Delta^3$-pyrroline
1-butyl-$\Delta^3$-pyrroline
there are obtained:
1-isopropyl-3,4-epoxypyrrolidine
1-methyl-3,4-epoxypyrrolidine
1-butyl-3,4-epoxypyrrolidine.

EXAMPLE 6

Following the procedure of Example 3, substituting molar equivalents of the following pyrrolines for 1-cyclohexyl-$\Delta^3$-pyrroline:
1-cyclopropyl-$\Delta^3$-pyrroline
1-cyclobutyl-$\Delta^3$-pyrroline
1-cyclopentyl-$\Delta^3$-pyrroline
there are obtained:
1-cyclopropyl-3,4-epoxypyrrolidine
1-cyclobutyl-3,4-epoxypyrrolidine 1-cyclopentyl-3,4-epoxypyrrolidine.

FORMULATION AND ADMINISTRATION

The invention further provides pharmaceutical compositions, as active ingredient, the novel compounds according to the invention in association with a pharmaceutical carrier or excipient. The compounds of Formula I and the pharmaceutically acceptable addition salts thereof may be presented in a form suitable for oral or parenteral administration. Thus, for example, compositions for oral administration are solid or liquid and can take the form of capsules, tablets, coated tablets, suspensions, etc., employing such carriers or excipients conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid, e.g., water or a parenterally acceptable oil, e.g., arachis oil, contained in ampoules.

Advantageously, the compositions are formulated as dosage units, each unit being adapted to supply a fixed effective dose of active ingredient. Unit dosages are usually from 5 milligrams or above and preferably 25, 50 or 100 milligrams. Obviously, several unit dosage forms may be administered at about the same time. Daily dosages vary from about 5 to 500 mg/kg/day active agent, preferably 25 to 350 mg/kg/day.

The following are examples formed in accordance with this invention.

(1) Capsules

Capsules of 5 mg., 25 mg., 50.0 mg. and 100.0 mg. of active ingredient per capsule are prepared.

| Typical blend of encapsulation | mg. per capsule |
|---|---|
| Active ingredient | 5.0 |
| Lactose | 140.0 |
| Starch | 40.0 |
| Total | 185.0 |

Uniformly blend the active ingredient with lactose and starch and encapsulate the blend.

Additional capsule formulations contain a higher dose of active ingredient and are as follows:

| Ingredients | 25 mg. per Capsule | 50 mg. per Capsule | 100 mg. per Capsule |
|---|---|---|---|
| Active ingredient | 25.0 | 50.0 | 100.0 |
| Lactose | 300.0 | 271.7 | 231.5 |
| Starch | 110.0 | 113.0 | 103.5 |
| Total | 435.0 | 435.0 | 435.0 |

(2) Tablets

A typical formulation for a tablet containing 5.0 mg. of active ingredient per tablet follows. The formulation may be used for other strengths of active ingredient by adjustment of weight of dicalcium phosphate.

| | Per tablet, mg. |
|---|---|
| (1) Active ingredient | 5.0 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 0.9 |
| Total | 170.1 |

Uniformly blend 1, 2, 4 and 5. Prepare 3 as 10 percent paste in water. Granulate the blend with starch paste and press the wet mass through an eight mesh screen. The wet granulation is dried and sized through a twelve mesh screen. The dried granules are blended with the calcium stearate and compressed.

Additional tablet formulations contain 25.0 mg., 50.0 mg. and 100.0 mg. of active ingredient per tablet. The tablets are prepared according to the foregoing formulation by adjustment of weight of dicalcium phosphate.

| INTRAMUSCULAR INJECTION | |
|---|---|
| Ingredients: | |
| 1. Active ingredient | mg. 5.0 |
| 2. Isotonic buffer solution 4.0, q.s. to | ml. 2.0 |

Procedure:

(1) Dissolve the active ingredient in the buffer solution.

(2) Aseptically filter the solution from No. 1.

(3) The sterile solution is now aseptically filled into sterile ampoules.

(4) The ampoules are sealed under aseptic conditions.

Various modifications and equivalents will be apparent to one skilled in the art and may be made in the compounds, compositions and methods of the present invention without departing from the spirit and scope thereof, and it is therefore understood that the invention is to be limited only by the scope of the appended claims.

What is claimed is:

1. A compound selected from 1-substituted-3,4-epoxypyrrolidines having the formula:

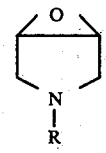

wherein R is loweralkyl, cycloalkyl having 3 to 9 carbon atoms or phenylalkyl wherein the alkyl moiety includes radicals of up to 4 carbon atoms and the acid addition salts thereof.

2. The compound of claim 1 which is 1-benzyl-3,4-epoxypyrrolidine oxalate.

3. The compound of claim 1 which is 1-benzyl-3,4-epoxypyrrolidine.

4. The compound of claim 1 which is 1-ethyl-3,4-epoxypyrrolidine oxalate.

5. The compound of claim 1 which is 1-ethyl-3,4-epoxypyrrolidine.

6. The compound of claim 1 which is 1-cyclohexyl-3,4-epoxypyrrolidine oxalate.

7. The compound of claim 1 which is 1-cyclohexyl-3,4-epoxypyrrolidine.

8. A method for the prevention or amelioration of diabetes complications consisting of cataracts in a diabetic animal which comprises administering to said animal an effective amount of a compound having the formula:

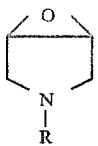

wherein R is loweralkyl, cycloalkyl having 3 to 9 carbon atoms or phenylalkyl wherein the alkyl moiety includes radicals of up to 4 carbon atoms and the pharmaceutically acceptable addition salts thereof.

9. A method of claim 8 wherein the compound is 1-benzyl-3,4-epoxypyrrolidine.

10. A method of claim 8 wherein the compound is 1-ethyl-3,4-epoxypyrrolidine.

11. A method of claim 8 wherein the compound is 1-cyclohexyl-3,4-epoxypyrrolidine.

12. A pharmaceutical composition for the prevention or amelioration of diabetic complications consisting of cataracts in a diabetic animal comprising (a) from 5 milligrams to 100 milligrams of a compound selected from 1-substituted -3,4-epoxypyrrolidines having the formula:

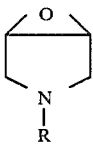

wherein R is loweralkyl, cycloalkyl having 3 to 9 carbon atoms or phenylalkyl wherein the alkyl moiety includes radicals of up to 4 carbon atoms and the pharmaceutically acceptable addition salts thereof, and (b) a pharmaceutically acceptable carrier.

13. A composition of claim 12 wherein the compound is 1-benzyl-3,4-epoxypyrrolidine oxalate.

14. A composition of claim 12 wherein the compound is 1-benzyl-3,4-epoxypyrrolidine.

15. A composition of claim 12 wherein the compound is 1-ethyl-3,4-epoxypyrrolidine oxalate.

16. A composition of claim 12 wherein the compound is 1-ethyl-3,4-epoxypyrrolidine.

17. A composition of claim 12 wherein the compound is 1-cyclohexyl-3,4-epoxypyrrolidine oxalate.

18. A composition of claim 12 wherein the compound is 1-cyclohexyl-3,4-epoxypyrrolidine.

19. A process for the preparation of 1-substituted-3,4-epoxypyrrolidines having the formula:

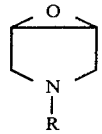

wherein R is loweralkyl, cycloalkyl and phenylalkyl which comprises the steps of (1) reacting a 1-substituted $\Delta^3$ pyrroline having the formula:

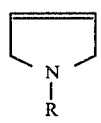

with chlorine in aqueous acidic medium to form 1-substituted-3-hydroxy-4-chloropyrrolidine having the formula:

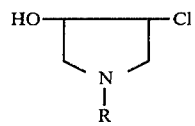

wherein R is as defined above and (2) causing epoxidation by reaction with base to form said 1-substituted-3,4-epoxypyrrolidines.

20. The process of claim 19 wherein 1-benzyl-$\Delta^3$-pyrroline is converted to 1-benzyl-3,4-epoxypyrrolidine.

21. The process of claim 19 wherein 1-ethyl-$\Delta^3$-pyrroline is converted to 1-ethyl-3,4-epoxypyrrolidine.

22. The process of claim 19 wherein 1-cyclohexyl-$\Delta^3$-pyrroline is converted to 1-cyclohexyl-3,4-epoxypyrrolidine.

* * * * *